United States Patent [19]

de Boer et al.

[11] Patent Number: 5,254,463
[45] Date of Patent: Oct. 19, 1993

[54] METHOD FOR EXPRESSION OF BOVINE GROWTH HORMONE

[75] Inventors: Herman A. de Boer, Pacifica; Herbert L. Heyneker, Burlingame; Peter H. Seeburg, San Francisco, all of Calif.

[73] Assignee: Genentech, Inc., South San Francisco, Calif.

[21] Appl. No.: 582,590

[22] Filed: Sep. 12, 1990

Related U.S. Application Data

[63] Continuation of Ser. No. 178,824, Apr. 5, 1988, abandoned, which is a continuation of Ser. No. 632,361, Jul. 19, 1984, abandoned, which is a continuation of Ser. No. 303,687, Sep. 18, 1981, abandoned.

[51] Int. Cl.$^5$ .................. C12P 21/02; C12N 15/71; C12N 15/70; C12N 15/03
[52] U.S. Cl. .................. 435/69.4; 435/252.3; 435/252.33; 435/320.1; 935/45
[58] Field of Search .................. 435/69.1–71.3, 435/91, 172.1, 172.3, 252.3–252.35, 320.1; 530/27; 935/10, 44, 45, 46, 61, 72, 73

[56] References Cited

U.S. PATENT DOCUMENTS

| | | | |
|---|---|---|---|
| 3,664,925 | 5/1972 | Sonnenberg | 435/68.1 |
| 4,356,270 | 10/1982 | Itakura | 435/320.1 |
| 4,443,539 | 4/1984 | Fraser et al. | 435/69.1 |

FOREIGN PATENT DOCUMENTS

| | | |
|---|---|---|
| 5949880 | 1/1981 | Australia . |
| 0001931 | 5/1979 | European Pat. Off. . |
| 022242 | 1/1981 | European Pat. Off. . |
| 0035914 | 9/1981 | European Pat. Off. . |
| 0047600 | 3/1982 | European Pat. Off. . |
| 0067026 | 12/1982 | European Pat. Off. . |
| 0068646 | 1/1983 | European Pat. Off. . |
| 0103395 | 3/1984 | European Pat. Off. . |
| 0120694 | 10/1984 | European Pat. Off. . |
| 0159123 | 10/1985 | European Pat. Off. . |
| 2007676 | 5/1979 | United Kingdom . |
| 2008123 | 5/1979 | United Kingdom . |
| 2024229 | 1/1980 | United Kingdom . |
| 2031434 | 4/1980 | United Kingdom . |
| 2033905 | 5/1980 | United Kingdom . |
| 2042554 | 9/1980 | United Kingdom . |
| 2069503 | 8/1981 | United Kingdom . |
| 2073245 | 10/1981 | United Kingdom . |
| 8607060 | 12/1986 | World Int. Prop. O. . |

OTHER PUBLICATIONS

Itakura et al., Science 198:1056–1063 (1977).
Sverdlov et al., Bioorganicheskaya Khimiya 5:112–15 (1979).
Korobko et al., Bioorganicheskaya Khimiya 5:1802–15 (1979).
Kumarev et al., FEBS Letters 114:273–277 (1980).
Wetzel et al., Biochemistry 19:6096–6104 (1980).
Horn et al., Nuc. Acids Res. Symp. Series 7;225–232 (1980).
Edge et al., Nature 292:756–762 (Aug. 1981).
Geysen et al., Gene 17:55–63 (1982).
Queen & Rosenberg, Cell 25:241–249 (1981).

(List continued on next page.)

Primary Examiner—James Martinell
Attorney, Agent, or Firm—Sean A. Johnston

[57] ABSTRACT

Microbial expression of an exogenous polypeptide may be inefficient if the messenger RNA has secondary structure (due to complementarity of spaced regions of the molecule) which impedes interaction with a ribosome. The occurrence of such structure can be predicted. The degeneracy of the genetic code gives freedom to alter the nucleic acid composition of the CDNA to eliminate harmful secondary structure of the MRNA.

For example, bovine growth hormone (BGH) is poorly expressed by E. coli transformed with a recombinant plasmid containing the natural BGH gene. The corresponding MRNA has complementary regions at 46–51 and 73–78. Therefore a plasmid PBGH 33-4 was constructed containing a BGH gene whose upstream portion was synthesized (making use of plasmid PHGH 207-1 which contains an efficiently expressible gene for the closely related human growth hormone) so as not to cause the troublesome complementarity. E. coli transformed therewith produced BGH with a yield of better than $10^5$ copies per cell.

26 Claims, 9 Drawing Sheets

OTHER PUBLICATIONS

Roberts, Promoters:Structure & Function, Rodrigues et al., Ed. 452–461 (1982).
Kozak, Current Topics in Microbio. & Immunol. 93:81–123 (1981).
Cannistraro & Kennell, Nature 277:407–409 (1979).
Shine et al., Nature 285:456–461 (1980).
Bahramian, J. Theor. Biol. 84:103–118 (1980).
Schoner et al., Proc. Natl. Acad. Sci. USA 81:5403–5407 (1984).
Drlica, Understanding DNA & Gene Cloning: A Guide for the Curious (1984).
Wetzel, American Scientist 68:664–675 (1980).
Miozzari, Recombinant DNA Tech. Bulletin 3(3):57–67 (1980).
Oxender et al., Proc. Natl. Acad. Sci. USA 76:5524–5528 (1979).
Min Jou et al., Nature 237:83–88 (1972).
Steitz Nature 224:957–964 (1969).
Steitz, RNA Phages, Zinder (Ed.) 319–352 (1975).
Seeburg et al., DNA 2:37–45 (1983).
Watson, Mol. Biol. of the Gene:World Student Series:3rd Ed. 208 & 11–357–75 (1976).
Dunn et al., Proc. Natl. Acad. Sci. USA 75:2741–2745 (1978).
Shepard et al., DNA 1:125–131 (1982).
Hudson et al., Nature 291:127–131 (1981).
Howard Florey Institute Annual Report, pp. 23–24 (1980).
Staden, Nuc. Acids Res. 5:1013–1015 (1978).
Backman & Ptashne Cell 13:65–71 (1978).
Zuker & Steigler Nuc. Acids Res. 9:133–149 (1981).
Kozak Cell 19:79–90 (1980).
Wieringa et al., Eur. J. Biochem. 114:635–641 (1981).
Talkad et al., J. Mol. Biol. 104:299–303 (1976).
Goeddel et al., P.N.A.S. 76: 106–110 (1979).
McIntyre et al., Eur. J. Biochem. 143:183–187 (1984).
Hudson et al., Nuc. Acids Res. 14: 5001–5013 (1986).
Keshet et al., Nuc. Acids. Res. 9;19–30 (1981).
Miller et al., J. Biol. Chem. 255:7521 (1980).
Miller et al., Ped. Res. 14:335 (1980).
Hall et al., Nature 295:616–618 (1982).
Goeddel et al., Nature 281:544–548 (1979).
Stebbing et al., Proc. 19th Ann. Miami Winter Symp., Academic Press N.Y. 445-58 (1982).
Steitz, Biol. Reg. & Dev., Goldberger(Ed.) 349–399 (1979).
Steege, Proc. Natl. Acad. Sci USA 74:4163–4167 (1977).
Steitz et al., P.N.A.S. 72:4734 (1975).
Iserentant, Gene 9:1–12 (1980).
Iserentant et al., Chem. Ab. 92:192883 (1980).
Tinoco et al., Nature New Biol. 246:40–41 (1973).
Singer et al., J. Mol. Biol. 149:405–432 (1981).
Gold et al., Ann. Rev. Microbiol., Starr et al. (Ed.) 35:388–403 (1981).
Guarente et al., Science 209:1428–1430 (1980).
Klambt et al., J. Theor. Biol. 58:319 (1976).
Johnston et al., Proc. Natl. Acad. Sci. USA 77:508 (1980).
Schwartz et al., Proc. Natl. Acad. Sci. USA 78: 2937–2941 (1981).
Machlin, J. Dairy Sci. 56: 575–580 (1973).
Dayhoff, Atlas of Prot. Ser & Str. 5:203 (1972).
Hudson et al., Proc. of Australian Biochem. Soc., vol. 14, abstr. of 25th Annual Mtg. of the Society Univ. of Adelaide, May 12–15, 1981.

```
BGH      ⎧ amino
natural  ⎨ acids:          Phe Pro Ala Met Ser Leu Ser Gly Leu Phe Ala Asn Ala Val Leu Arg Ala Gln His Leu His Gln
         ⎩ bases:          TTC CCA GCC ATG TCC TTG TCC GGC CTG TTT GCC AAC GCT GTG CTC CGG GCT CAG CAC CTG CAT CAG
                                                                                                               PvuII HGH      ⎧ amino
synthetic⎨ acids:  Met Phe Pro Thr Ile Pro Leu Ser Arg Leu Phe Asp Asn Ala Met Leu Arg Ala His Arg Leu His Gln
         ⎩ bases:  ATG TTC CCA ACT ATA CCA CTA TCT CGT CTA TTC GAT AAC GCT ATG CTT CGT GCT CAT CGT CTT CAT CAG
                                                                                                           PvuII BGH      ⎧ amino
synthetic⎨ acids:  Met Phe Pro Ala Met Ser Leu Ser Gly Leu Phe Ala Asn Ala Val Leu Arg Ala Gln His Leu His Gln
         ⎩ bases:  ATG TTC CCA GCT ATG TCT CTA TCT GGT CTA TTC GCT AAC GCT GTT CTT CGT GCT CAG CAT CTT CAT CAG
                                                                                                           PvuII
```

FIG. I

|  | Natural BGH | | | | Synthetic BGH | | | |
|---|---|---|---|---|---|---|---|---|
| 5' | 3' | length | kcal/mol | 5' | 3' | length | kcal/mol |
| 14 | 45 | 8 | −11.80 | 14 | 79 | 7 | −5.50 |
| 16 | 31 | 6 | 4.00 | 16 | 37 | 6 | −4.00 |
| 33 | 101 | 6 | −15.40 | 38 | 104 | 6 | −15.40 |
| 46 | 78 | 6 | −15.20 | 52 | 84 | − | >−10 |

FIG. 3

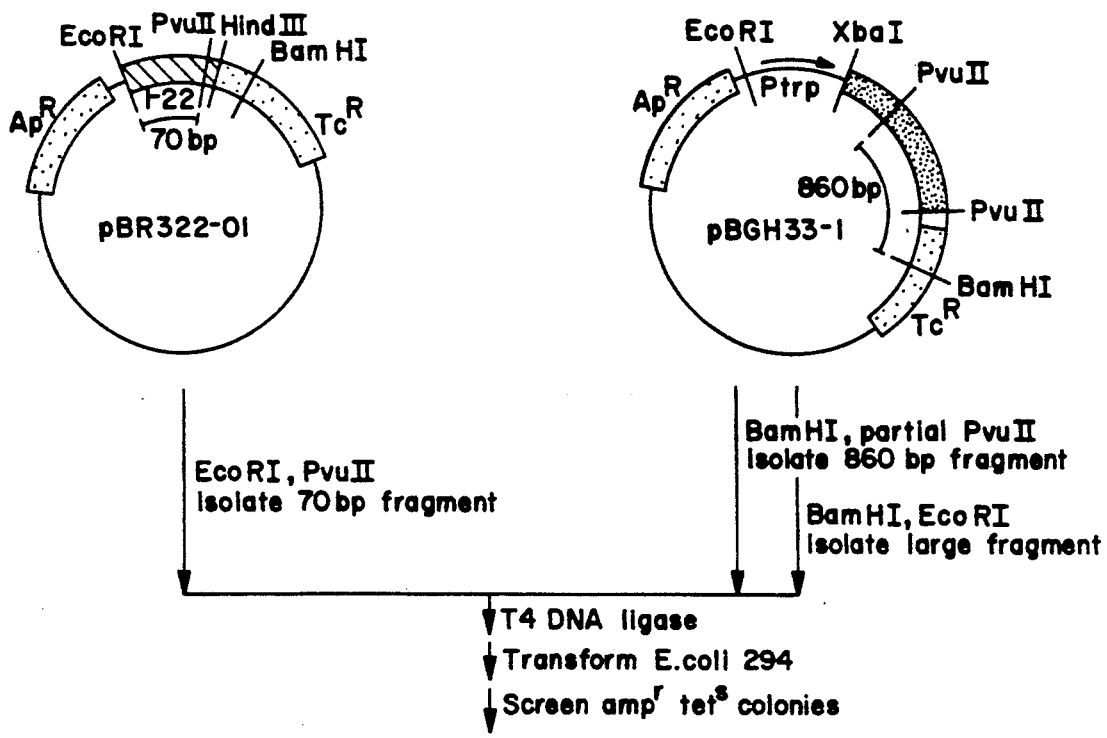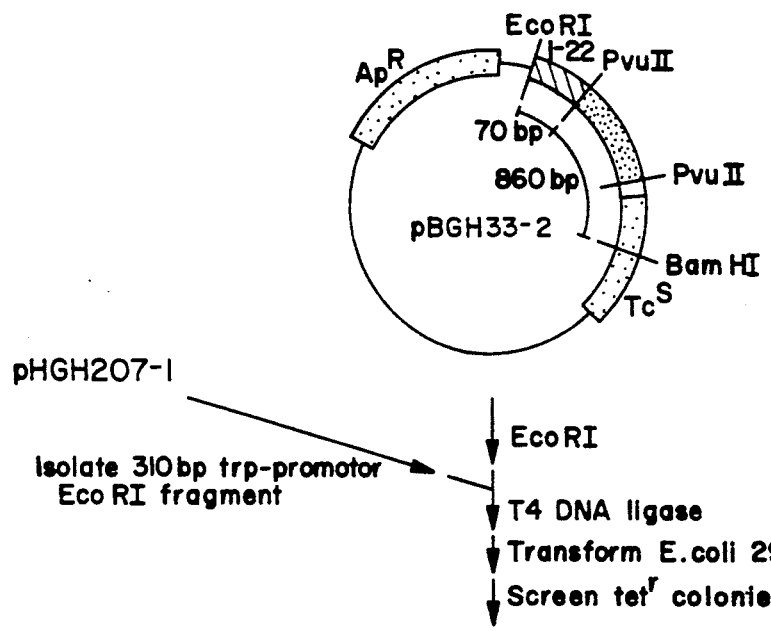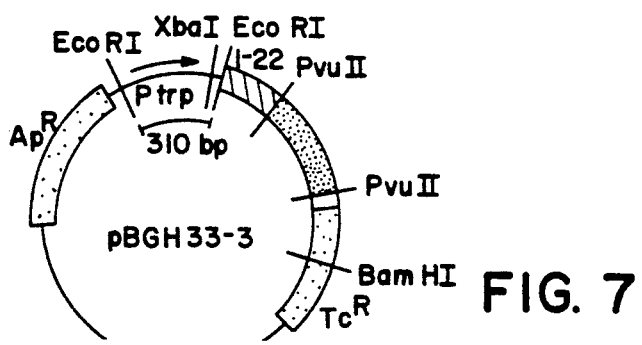
FIG. 7

METHOD FOR EXPRESSION OF BOVINE GROWTH HORMONE

This application is a continuation of application Ser. No. 07/178,824, filed Apr. 5, 1988 (now abandoned), which is a continuation of application Ser. No. 06/632,361, filed Jul. 19, 1984 (now abandoned), which is a continuation of application Ser. No. 06/303687, filed Sep. 18, 1981 (now abandoned).

FIELD OF THE INVENTION

The present invention provides methods and means for preparing DNA sequences that provide messenger RNA having improved translation characteristics. In accordance herewith, such improved messenger RNA is highly efficient in translation to give substantial amounts of polypeptide product that is normally heterologous to the host microorganism. The DNA sequences which are ultimately expressed, that is, transcribed into messenger RNA (MRNA) which is in turn translated into polypeptide product, are, in essential part, synthetically prepared, in accordance with this invention, utilizing means that favor the substantial reduction or elimination of secondary and/or tertiary structure in the corresponding transcribed MRNA. An absence or substantial reduction in such secondary/tertiary structure involving tile 5' end of MRNA permits effective recognition and binding of ribosomes(s) to the MRNA for subsequent translation. Thus, the efficiency of translation is not hindered or impaired by conformational impediments in the structure of the transcribed mRNA. Methods and means for measuring MRNA secondary/tertiary structure are also described as well as associated means designed to insure that secondary/tertiary structure is kept below certain preferred limits. This invention is exemplified by the preparation of various preferred protein products.

BACKGROUND OF THE INVENTION

A. Recombinant DNA Technology

With the advent of recombinant DNA technology, the controlled microbial production of an enormous variety of useful polypeptides has become possible, putting within reach the microbially directed manufacture of hormones, enzymes, antibodies, and vaccines useful against a wide variety of diseases. Many mammalian polypeptides, such as human growth hormone and leukocyte interferons, have already been produced by various microorganisms.

One basic element of recombinant DNA technology is the plasmid, an extrachromosomal loop of double-stranded DNA found in bacteria oftentimes in multiple copies per cell. Included in the information encoded in the plasmid DNA is that required to reproduce the plasmid in daughter cells (i.e., a "replicon") and ordinarily, one or more selection characteristics, such as resistance to antibiotics, which permit clones of the host cell containing the plasmid of interest to be recognized and preferentially grown in selective media. The utility of such bacterial plasmids lies in the fact that they can be specifically cleaved by one or another restriction endonuclease or "restriction enzyme", each of which recognizes a different site on the plasmidic DNA. Heterologous genes or gene fragments may be inserted into the plasmid by endwise joining at the cleavage site or at reconstructed ends adjacent to the cleavage site. (As used herein, the term "heterologous" refers to a gene not ordinarily found in, or a polypeptide sequence ordinarily not produced by, a given microorganism, whereas the term "homologous" refers to a gene or polypeptide which is found in, or produced by the corresponding wild-type microorganism.) Thus formed are so-called replicable expression vehicles.

DNA recombination is performed outside the microorganism, and the resulting "recombinant" plasmid can be introduced into microorganisms by a process known as transformation and large quantities of the heterologous gene-containing recombinant plasmid are obtained by growing the transformant. Moreover, where the gene is properly inserted with reference to portions of the plasmid which govern the transcription and translation of the encoding DNA, the resulting plasmid can be used to actually produce the polypeptide sequence for which the inserted gene codes, a process referred to as expression. Plasmids which express a (heterologous) gene are referred to as replicable expression vehicles.

Expression is initiated in a DNA region known as the premotor. In some cases, as in the lac and trp systems discussed infra, premotor regions are overlapped by "operator" regions to form a combined premotor-operator. Operators are DNA sequences which are recognized by so-called repressor proteins which serve to regulate the frequency of transcription initiation from a particular promoter. In the transcription phase of expression, RNA polymerase recognizes certain sequences in and binds to the promoter DNA. The binding interaction causes an unwinding of the DNA in this region, exposing the DNA as a template for synthesis of messenger RNA Tile messenger RNA serves as a template for ribosomes which bind to the messenger RNA and translate the MRNA into a polypeptide chain having the amino acid sequence for which the RNA/DNA codes. Each amino acid is encoded by a nucleotide triplet or "codon" which collectively make up the "structural gene", i.e.t that part of the DNA sequence which encodes the amino acid sequence of the expressed polypeptide product.

After binding to the promoter, RNA Polymerase initiates the transcription of DNA encoding a ribosome binding site including a translation initiation or "start" signal (ordinarily ATG, which in the resulting messenger RNA becomes AUG), followed by DNA sequences encoding the structural gene itself. So-called translational stop codons are transcribed at the end of the structural gene whereafter the polymerase may form an additional sequence of messenger RNA which, because of the presence of the translational stop signal, will remain untranslated by the ribosomes. Ribosomes bind to the binding site provided on the messenger RNA, in bacteria ordinarily as the MRNA is being formed, and direct subsequently the production of the encoded Polypeptide, beginning at the translation start Signal and ending .at the previously mentioned retop signal(s). The resulting product may be obtained by lysing the host cell and recovering the product by appropriate Purification from other bacterial proteins.

Polypeptides expressed through the use of recombinant DNA technology may be entirely heterologous, functional proteins, as in the case of the direct expression of human growth hormone, or alternatively may comprise a bioactive heterologous polypeptide portion and, fused thereto, a portion of the amino acid sequence of a homologous polypeptide, as in the case of the production of intermediates for somatostatin and the components of human insulin. In the latter cases, for example, the fused homologous polypeptide comprised a portion of the amino acid sequence for beta galactosidase. In those cases, the intended bioactive product is rendered bioinactive within the fused, homologous/heterologous polypeptide until it is cleaved in an extracellular environment. Fusion proteins like those just mentioned can be designed so as to permit highly specific cleavage of the precursor protein from the intended product, as by the action of cyanogen bromide on methionine, or alternatively by enzymatic cleavage. See, eg., G.B. Patent Publication No. 2 007 676 A.

If recombinant DNA technology is to fully sustain its promise, systems must be devised which optimize expression of gene inserts, so that the intended polypeptide products can be made available in controlled environments and in high yields.

B. Promoter Systems

As examples, the beta lactamase and lactose promoter systems have been advantageously used to initiate and sustain microbial production of heterologous polypeptides. Details relating to the make-up and construction of these promoter systems have been published by Chang et al., Nature 275, 617 (1978) and Itakura et al., Science 198, 1056 (1977), which are hereby incorporated by reference. More recently, a system based upon tryptophan, the so-called trp promoter system, has been developed. Details relating to the make-up and construction of this system have been published by Goeddel et al., Nucleic Acids Research 8, 4057 (1980) and Kleid et al., U.S. Ser. No. 133, 296, filed Mar. 24, 1980, which are hereby incorporated by reference. Numerous other microbial promoters have been discovered and utilized and details concerning their nucleotide sequences, enabling a skilled worker to ligate them functionally within plasmid vectors, have been published—see, e.g., Siebenlist et al., Cell 20, 269 (1980), which is incorporated herein by this reference.

C. Background Art

Historically, recombinant cloning vehicles (extrachromosomal duplex DNA having, inter alia., a functional origin of replication) have been prepared and used to transform microorganisms—cf. Ullrich et al., Science 196, 1313 (1977). Later, there were attempts to actually express the DNA gene inserts encoding a heterologous polypeptide. Itakura et al. (Science 198, 1056 (1977)) expressed the gene encoding somatostatin in E. coli. Other like successes followed, the gene inserts being constructed by organic synthesis using newly refined technology. In order, among other things, to avoid possible proteolytic degradation of the polypeptide product within the microbe, the genes were ligated to DNA sequences coding for a precursor polypeptide. Extracellular cleavage yielded the intended protein product, as discussed above.

In the case of larger proteins, chemical synthesis of the underlying DNA sequence proved unwieldy. Accordingly, resort was had to the preparation of gene sequences by reverse transcription from corresponding messenger RNA obtained from requisite tissues and/or culture cells. These methods did not always prove satisfactory owing to the termination of transcription short of the entire sequence and/or the desired sequence would be accompanied by naturally occurring precursor leader or signal DNA. Thus, these attempts often have resulted in incomplete protein product and/or protein product in non-cleavable conjugate form—cf. Villa-Komaroff et al., Proc. Natl. Acad. Sci. (USA) 75, 3727 (1978) and Seeburg et al., Nature 276, 795 (1978).

In order to avoid these difficulties, Goeddel et al., Nature 281, 544 (1979), constructed DNA, inter alia. encoding human growth hormone, using chemically synthesized DNA in conjunction with enzymatically synthesized DNA. This discovery thus made available the means enabling the microbial expression of hybrid DNA (combination of chemically synthesized DNA with enzymatically synthesized DNA), notably coding for proteins of limited availability which would probably otherwise not have been produced economically. The hybrid DNA, encoding heterologous polypeptide is provided in substantial portion, preferably a majority, via reverse transcription of MRNA while the remainder is provided via chemical synthesis. In a preferred embodiment, synthetic DNA encoding the first 24 amino acids of human growth hormone (HGH) was constructed according to a plan which incorporated an endonuclease restriction site in the DNA corresponding to HGH amino acids 23 and 24. This was done to facilitate a connection with downstream HGH CDNA sequences. The various 12 oligonucleotide long fragments making up the synthetic part of the DNA were chosen following then known criteria for gene synthesis: avoidance of undue complementarity of the fragments, one with another, except, of course, those destined to occupy opposing sections of the double stranded sequence; avoidance of AT rich regions to minimize transcription termination; and choice of "microbially preferred codons." Following synthesis, the fragments were permitted to effect complimentary hydrogen bonding and were ligated according to methods known per se. This work is described U.S. Pat. No. 4,342,832 which is hereby incorporated by this reference.

While the successful preparation and expression of such hybrid DNA provided a useful means for preparing heterologous polypeptides, it did not address the general problem that eucaryotic genes are not always recognized by procaryotic expression machinery in a way which provides copious amounts of end product. Evolution has incorporated sophistication unique to discrete organisms. Bearing in mind that the eukaryotic gene insert is heterologous to the prohoryotic organism, the relative inefficiency in expression often observed can be true for any gene insert whether it is produced chemically, from CDNA or as a hybrid. Thus, the criteria used to construct the synthetic part of the gene for HGH, defined above, are not the sole factors influencing expression levels. For example, concentrating on codon choice as the previous workers have done—cf. British Patent Specification 2007676 A—has not been completely successful in raising the efficiency of expression towards maximal expression levels.

Guarante et al., Science 209, 1428 (1980) experimented with several hybrid ribosome binding sites, designed to match the number of base pairs between the Shine-Delgarno sequence and the ATG of some known E. coli binding sites, their work suggesting that the reason(s) for observed relatively low efficiencies of eucaryotic gene expression by procaryote organisms is more subtle.

That the initiation of MRNA translation may be a multicomponent process is illustrated by work reported by Iserentant and Fiers, Gene 9, 1 (1980). They postulate that secondary structure of MRNA is one of the components influencing translation efficiency and imply that the initiation codon and ribosome interaction site of secondary structured, folded MRNA must be "accessible." However, what those workers apparently mean by "accessible" is that the codon and site referred to be located on the loop, rather than the stem, of the secondary structure models they have hypothesized.

The present invention is based upon the discovery that the presence of secondary/tertiary conformational structure in the mRNA interferes with the initiation and maintenance of ribosomal binding during the translation phase of heterologous gene expression.

The present invention, relating to these findings, uniquely provides methods and means for providing efficient expression of heterologous gene inserts by the requisite microbial host. The present invention is further directed to a method of microbially producing heterologous polypeptides, utilizing specifically tailored beterologous gene inserts in microbial expression vehicles, as well as associated means. It is particularly directed to the use of synthetically derived gene insert portions that are prepared so as to both encode the desired polypeptide product and provide MRNA that has Lnininal secondary/ tertiary structure and hence is accessible for efficient ribosomal translation.

SUMMARY OF THE INVENTION

According to the present invention, synthetic DNA is provided for a substantial portion of the initial coding sequence of a heterologous gene insert, and optionally, upstream therefrom through the ATG translational start codon and ribosome binding site. The critical portion of DNA is chemically synthesized, keeping in mind two factors: 1) the creation of a sequence that codes for the initial (N-terminus) amino acid sequence of a polypeptide comprising a functional protein or bioactive portion thereof and 2) the assurance that said sequence provides, on transcription, messenger RNA that has a secondary/tertiary conformational structure which is insufficient to interfere with its accessibility for efficient ribosomal translation, as herein defined. Such chemical synthesis includes standard organic synthesis using modified mononucleotides as building blocks such as according to the method of Crea et al., *Nucleic Acids Research* 8, 2331 (1980) as well as the use of site directed mutagenesis of DNA fragments such as according to the method of Razin et al., *Proc. Natl. Acad Sci* (USA) 75, 4268 (1978) and the use of synthetic primers on certain appropriately sequenced DNA fragments followed by specific cleavage of the desired region..

The present invention is directed to a process of preparing DNA sequences comprising nucleotides arranged sequentially so as to encode the proper amino acid sequence of a given polypeptide.

This method involves the obtainment of a substantial portion of the DNA coding sequence of a given polypeptide via means other than chemical synthesis, most often by reverse transcription from requisite tissue and/or culture cell messenger RNA. This fragment encodes the C-terminal portion of the polypeptide and is ligated, in accordance herewith to a remainder of the coding sequence, obtained by chemical synthesis, optionally including properly positioned translational start and stop signals and upstream DNA through the ribosome binding site and the first nucleotide (+1) of the resultant messenger RNA. The synthetic fragment is designed by nucleotide choice dependent on conformation of the corresponding messenger RNA according to the criteria as herein discussed.

The such prepared DNA sequences are suited for insertion and use in replicable expression vehicles designed to direct the production of the heterologous polypeptide in a transformant microorganism. In these vehicles, the DNA sequence is operably linked to promotor systems which control its expression. The invention is further directed to the replicable expression vehicles and the transformant microorganisms so produced as well as to cultures of these microorganisms in customary fermentation media. This invention is further directed to associated methods and means and to specific embodiments for the directed production of messenger RNA transcripts that are accessible for efficient ribosomal translation.

Specifically excluded from the present invention is the hybrid DNA encoding human growth hormone (HGH) as disclosed by Goeddel et al., *Nature* 281, 544 (1979). While this particular hybrid DNA was successfully expressed to produce the intended product, the concept of the present invention was not appreciated by these workers (and hence not taught by them) and consequently was not practiced in the fortuitous preparation of their expressible hybrid DNA for HGH. This hybrid DNA has the following sequence (Table 1):

TABLE I

```
      1
met   phe   pro   thr   ile   pro   leu   ser   arg   leu   phe   asp   asn   ala   met
ATG   TTC   CCA   ACT   ATA   CCA   CTA   TCT   CGT   CTA   TTC   GAT   AAC   GCT   ATG 20
leu   arg   ala   his   arg   leu   his   gln   leu   ala   phe   asp   thr   tyr   gln
CTT   CGT   GCT   CAT   CGT   CTT   CAT   CAG   CTG   GCC   TTT   GAC   ACC   TAC   CAG 40
glu   phe   glu   glu   ala   tyr   ile   pro   lys   glu   gln   lys   tyr   ser   phe
GAG   TTT   GAA   GAA   GCC   TAT   ATC   CCA   AAG   GAA   CAG   AAG   TAT   TCA   TTC leu   gln   asn   pro   gln   thr   ser   leu   cys   phe   ser   glu   ser   ile   pro
CTG   CAG   AAC   CCC   CAG   ACC   TCC   CTC   TGT   TTC   TCA   GAG   TCT   ATT   CCG 60
thr   pro   ser   asn   arg   glu   glu   thr   gln   gln   lys   ser   asn   leu   glu
ACA   CCC   TCC   AAC   AGG   GAG   GAA   ACA   CAA   CAG   AAA   TCC   AAC   CTA   GAG 80
leu   leu   arg   ile   ser   leu   leu   leu   ile   gln   ser   trp   leu   glu   pro
CTG   CTC   CGC   ATC   TCC   CTG   CTG   CTC   ATC   CAG   TCG   TGG   CTG   GAG   CCC
```

TABLE I-continued

```
                                            100
val  gln  phe  leu  arg  ser  val  phe  ala  asn  ser  leu  val  tyr  gly
GTG  CAG  TTC  CTC  AGG  AGT  GTC  TTC  GCC  AAC  AGC  CTA  GTG  TAC  GGC ala  ser  asp  ser  asn  val  tyr  asp  leu  leu  lys  asp  leu  glu  glu
GCC  TCT  GAC  AGC  AAC  GTC  TAT  GAC  CTC  CTA  AAG  GAC  CTA  GAG  GAA 120
gly  ile  gln  thr  leu  met  gly  arg  leu  glu  asp  gly  ser  pro  arg
GGC  ATC  CAA  ACG  CTG  ATG  GGG  AGG  CTG  GAA  GAT  GGC  AGC  CCC  CGG 140
thr  gly  gln  ile  phe  lys  gln  thr  tyr  ser  lys  phe  asp  thr  asn
ACT  GGG  CAG  ATC  TTC  AAG  CAG  ACC  TAC  AGC  AAG  TTC  GAC  ACA  AAC 160
ser  his  asn  asp  asp  ala  leu  leu  lys  asn  tyr  gly  leu  leu  tyr
TCA  CAC  AAC  GAT  GAC  GCA  CTA  CTC  AAG  AAC  TAC  GGG  CTG  CTC  TAC cys  phe  arg  lys  asp  met  asp  lys  val  glu  thr  phe  leu  arg  ile
TGC  TTC  AGG  AAG  GAC  ATG  GAC  AAG  GTC  GAG  ACA  TTC  CTG  CGC  ATC 180                                                      191
val  gln  cys  arg  ser  val  glu  gly  ser  cys  gly  phe  stop
GTG  CAG  TGC  CGC  TCT  GTG  GAG  GGC  AGC  TGT  GGC  TTC  TAG
```

The chemically synthetic DNA sequences hereof extend preferably from the ATG translation initiation site, and optionally upstream therefrom a given distance upwards of through the transcription initiation site (labelled +1 by convention), and then to sequences downstream encoding a substantial part of the desired polypeptide. By way of preference, the synthetic DNA comprises upwards of approximately 75 or more nucleotide pairs of the structural gene representing about the proximal (N-terminal) 25 amino acids of the intended polypeptide. In particularly preferred embodiments, the synthetic DNA sequence extends from about the translation initiation site (ATG) to about nucleotide 75 of the heterologous gene. In alternative terms, the synthetic DNA sequence comprises nucleotide pairs from +1 (transcription initiation) to about nucleotide 100 of the transcript.

Because of the degeneracy of the genetic code, there is substantial freedom in codon choice for any given amino acid sequence. Given this freedom, the number of different DNA nucleotide sequences encoding any given amino acid sequence is exceedingly large, for example, upwards of $2.6 \times 10^5$ possibilities for somatostatin consisting of only 14 amino acids. Again, the present invention provides methods and ifeans for selecting certain of these DNA sequences, those which will efficiently prepare functional product. For a given polypeptide product hereof, the present invention provides means to select, from among the large number possible, those DNA sequences that provide transcripts, the conformational structure of which admits of accessibility for operable and efficient ribosomal translation.

Conformational structure of MRNA transcripts is a consequence of hydrogen bonding between complementary nucleotide sequences that may be separated one from another by a sequence of noncomplementary nucleotides. Such bonding is commonly referred to as secondary structure. So-called tertiary structures may add to the conformation of the overall molecule. These structures are believed to be a result of spatial. Interactions within one or more portions of the molecule—so-called stacking interactions. In any event, the conformational structure of a given MRNA molecule can be determined and measured. Further, it was determined, according to this invention, that certain levels of conformational structure of URNA transcripts interfere with efficient protein synthesis, thus effectively blocking the initiation and/or continuation of translation (elongation) into polypeptide product. Accordingly, levels at which such conformational structure does not occur, or at least is minimal, can be predicted. Nucleotide choice can be prescribed on the basis of the predictable, permissible levels of conformational structure, and preferred gene sequences determined accordingly.

The measurement of MRIJA conformational structure is determined, in accordance herewith, by measuring the energy levels associated with the conformational structure of the MRIJA molecule.

In determining such energy levels, the thermodynamic disassociation energy connected with one or a series of homologous base pairings are calculated, for example according to the rules of Tinoco et al., Nature New Biol 246, 40(1973). In this calculation, as applied to the DNA sequence encoding a particular mRNA molecule, AT base pairing is assigned an associated energy level of about $-1.2$ Kcal/mole while a CG base pairing is assigned as associated energy level of about $-2$ Kcal/mole. Adjacent homologous pairings are more than additive, doubtless due to stacking interactions and other associative factors. In any event, it has been determined that in those instances where regional base pairing interactions result in energy levels upwards from about the interfering free energy levels of the (that is, structures described herein values expressed arithmetically in numbers less than about the interfering free energy levels of the structures described herein) for a given homologous sequence, such interactions are likely sufficient to binder or block the translation phase of expression, most probably by internal ring with accessibility for necessary ribosomal binding.

A given DNA sequence is screened as follows: A first series of base pairs, e.g., approximately the first six base pairs, are compared for homology with the corresponding reverse last base pairs of the gene. If such homology is found, the associate energy levels are calculated according to the above considerations. The first series of base pairs is next compared with the corresponding last base pairs up to the penultimate base pair of the gene and the associative energy levels of any homology calculated. In succession the first series of base pairs is next compared with the corresponding number of base pairs up to the antipenultimate base pair, and so on until the entire gene sequence is compared, back to front. Next, the series of base pairs beginning one downstream from the first series, e.g. base pairs 2 to 7 of the prior example, is compared with the corresponding number from the end and progressively toward the front of the gene, as described above. This procedure is repeated until each base pair is compared for homology with all other regions of the gene and associated energy levels are determined. Thus, for example in FIG. 3 there are provided results of such scanning and calculating for two genes - those encoding natural bovine growth hormone (BGH) and synthetic (i.e., hybrid) BGH. It can be seen that natural BW contains two regions of homology considered relevant herein to wit, six base pairs from base pair 33 to 38 with homologous pairs 96 to 101 and six base pairs from 46 to 51 with 73 to 743. The first is not significant for present purpose, despite the energy level (15.40 kcal/mole), presumably because the legion of homology lies downstream a sufficient distance so as not to be influential to translation efficiency. The second region is significant as evidenced by the poor yields of product as described herein cf. infra. The synthetic BGH gene where such region of homology was eliminated provided good yields of intended protein.

BRIEF DESCRIPTION OF THE DRAWINGS

FIG. 1 depicts the amino acid and nucleotide sequences of the proximal portions of a natural BGH, synthetic HGH, and synthetic BGH. The amino acids and nucleotides in natural BGH that are different from those in synthetic HGH are underlined. The nucleotides in the proximal portion of the synthetic BGH gene that differ from those in natural BGH gene also are underlined. The position of the PvuII restriction site at the end of the proximal portion of these genes is indicated.

In arriving at the synthetic BGH gene encoding the proper amino acid sequence for BGH, the nucleotide sequences of natural BGH and synthetic HGH were compared. Nucleotide selections were made based upon the synthetic HGH gene for construction of the synthetic BGH gene taking into account also the latitude permitted by the degeneracy of the genetic code, using a minimum of nucleotide changes from the synthetic HGH sequence.

Figure 2:
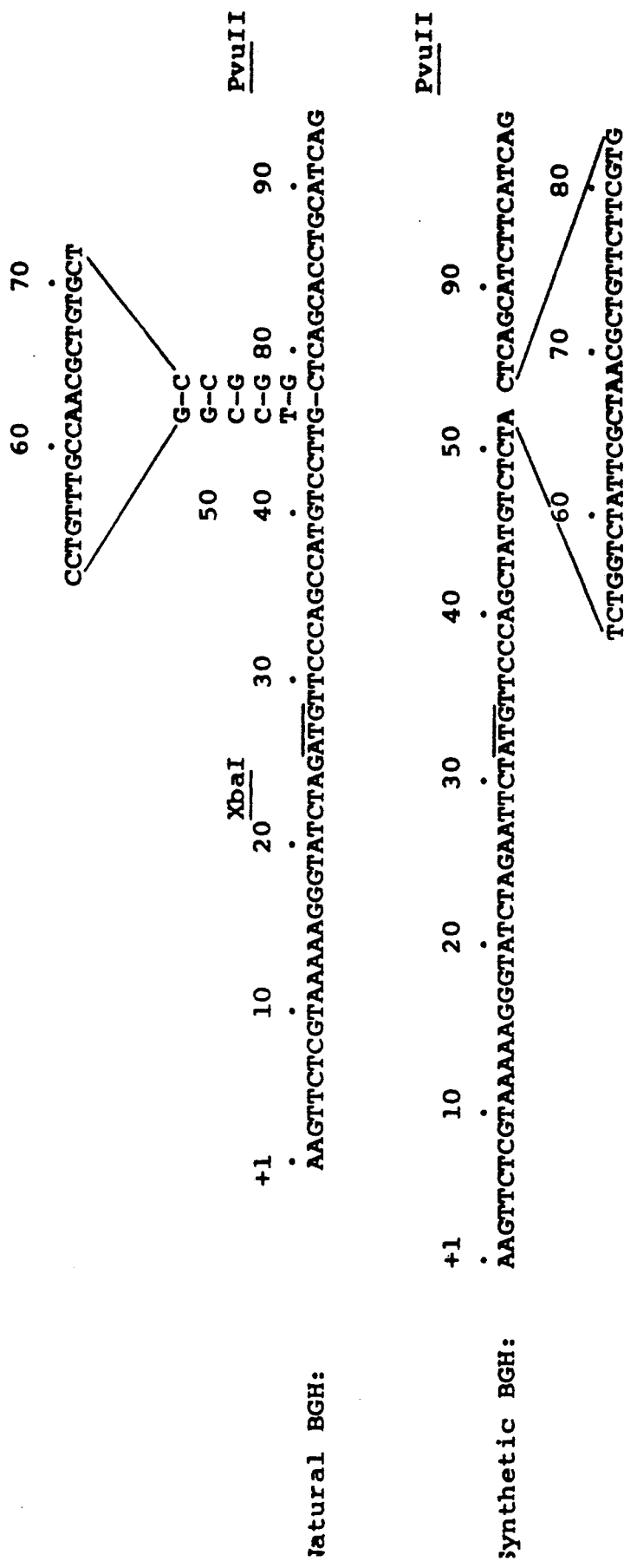

FIG. 2 depicts the nucleotide sequences of the sense strands of both natural and synthetic BGH genes along with the transcribed portions of the respective preceding trp-promotor sequences. The first nucleotide of each transcript is indicated as "+1" and the following nucleotides are numbered sequentially. The sequences are lined up to match the translated coding regions of both genes, beginning at the start codon "ATG" of each (overlined). The transcript of the natural BGH gene shows an area of "secondary structure" due to interactions cf nucleotides 46 to 51 with nucleotides 73 to 78, respectively (see FIG. 3). thus creating the stem-loop structure depicted. This area is not present in the synthetic BGH gene, removed by virtue of nucleotide changes (see FIG. 1), which nevertheless retains the correct amino acid sequence.

FIG. 3 shows the locations and stabilities of secondary structures in the transcripts of natural and synthetic BGH. (See FIG. 2) These locations and stabilities were determined using a nucleotide by nucleotide analysis, as described herein. Each area of significant secondary structure of each proximal portion of gene is listed in the respective table. Thus, for natural BGH versus synthetic BGH, it is noted that the energy levels of "secondary structure" at corresponding portions of the translatable transcripts (namely, nucleotides 46 to 78 comprising a 6 nucleotide long stem in natural BGH versus nucleotides 52 to 84 of synthetic BGH) are markedly different (15.2 kcal/mole versus greater than 10 kcal/mole), accounting for the observed success of expression of the synthetic BGH gene versus the natural BGH gene, cf. infra. The energy levels indicate the significance of the relative amounts of tolerable "secondary structure", based upon thermodynamic energy considerations. The significance of location of "secondary structure" can be appreciated by the fact that energy levels calculated for positions 33 to 101 versus 38 to 104 of natural versus synthetic BGH, respectively, did not significantly influence expression levels.

Figure 4:
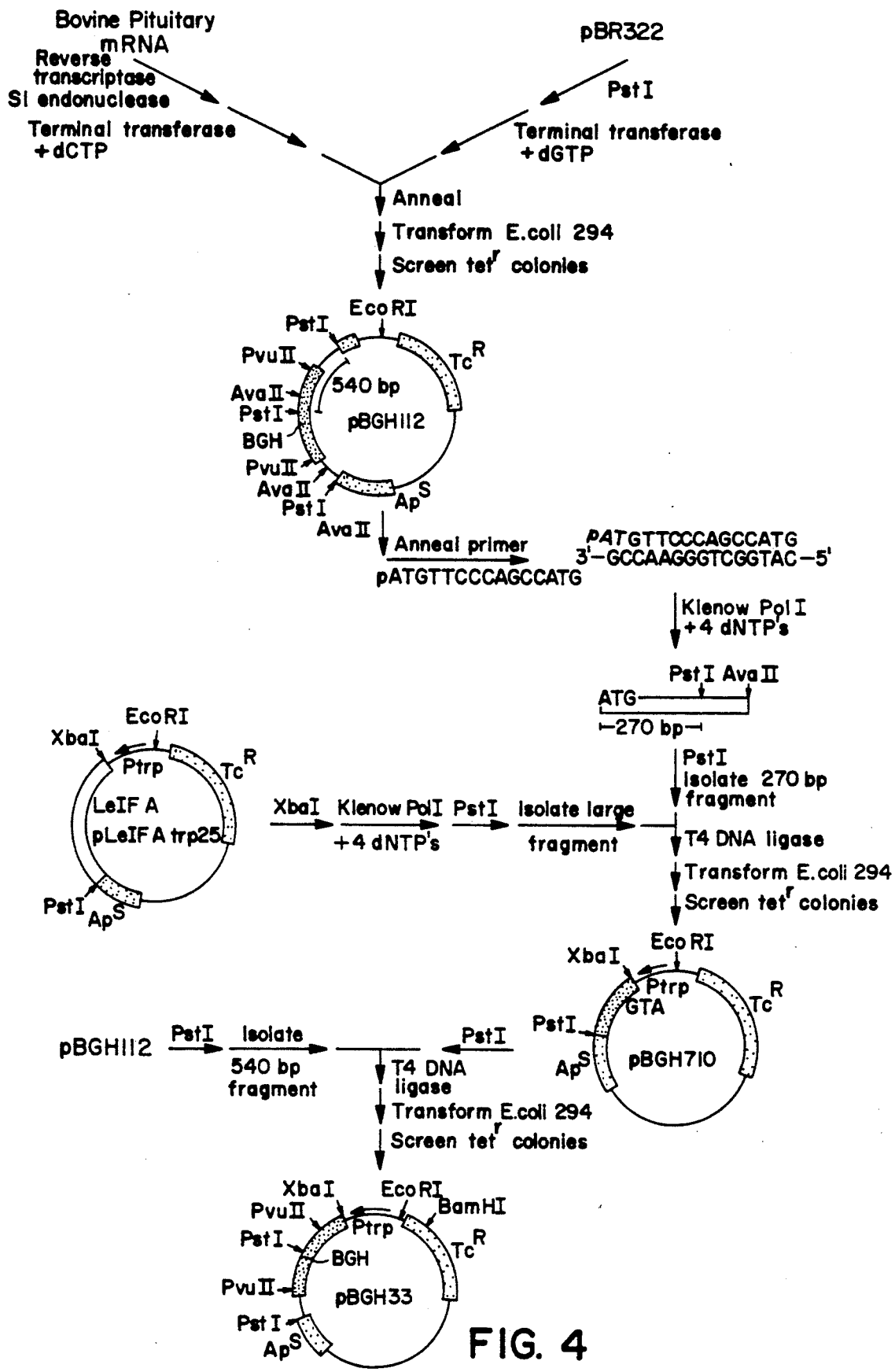
Figure 5:
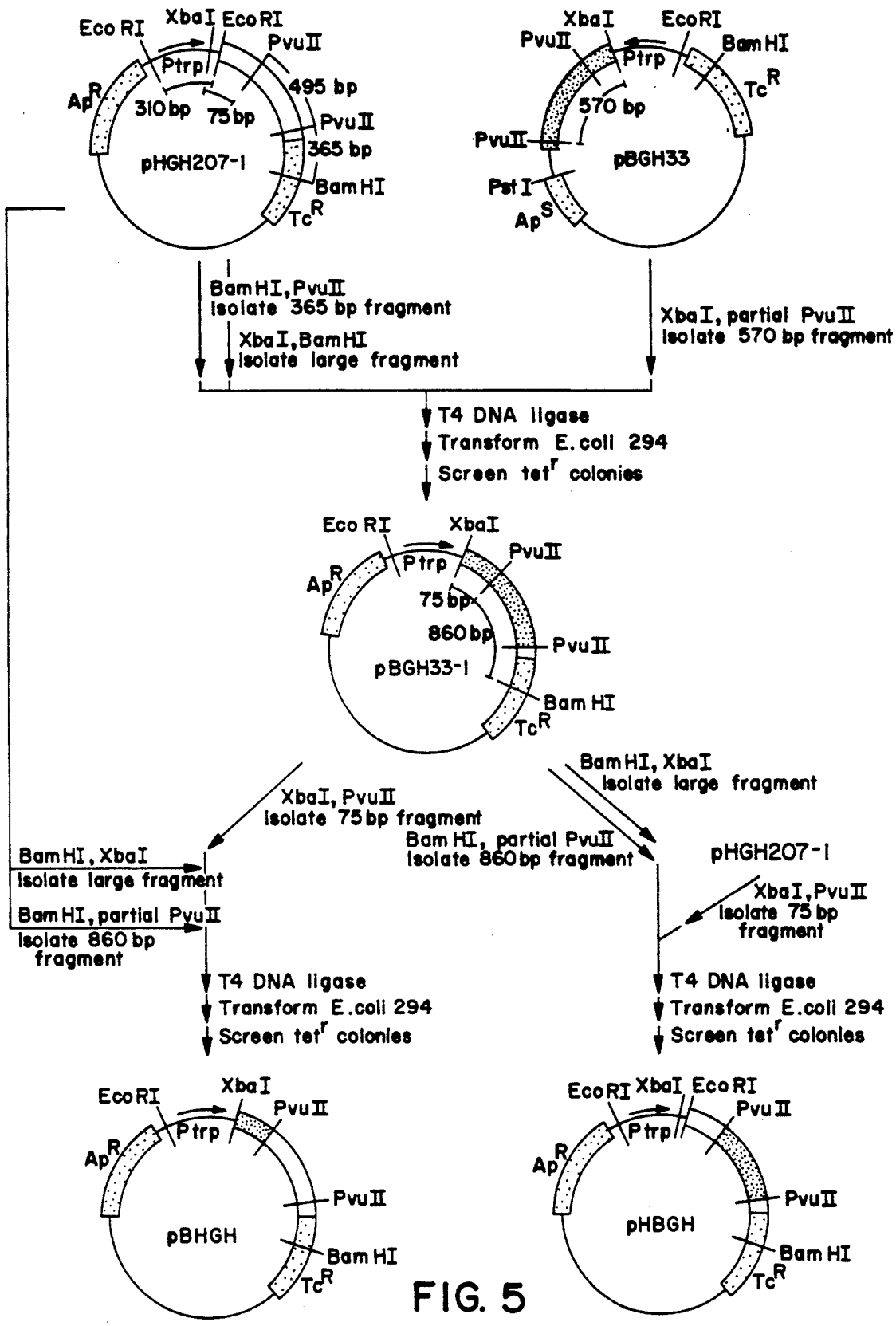

FIG. 4 depicts the construction of PBGH 33 used as shown in FIG. 5.

FIG. 5 depicts the construction cf plasmids harboring DNA sequences for hybrid polypeptides: PBHGH 33-1 used as shown in FIG. 7, PBHGH, being a hybrid of bovine and human growth hormone sequences, and PHBGH, a hybrid of human and bovine sequences.

Figure 6:
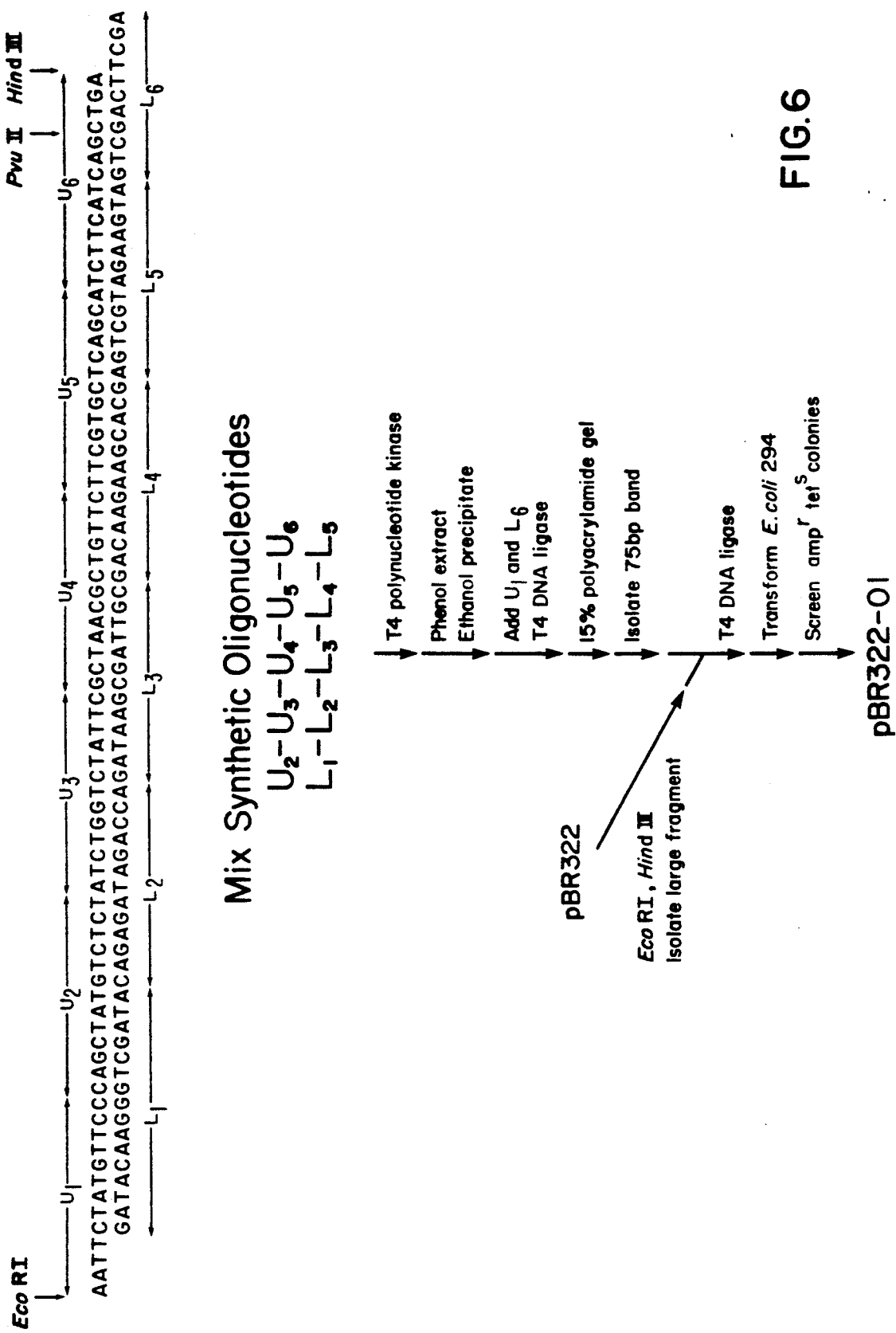

FIG. 6 depicts the technique used to assemble the synthetic proximal portion of the BGH gene, pBR 322-01, used in the construction shown in FIG. 7.

FIG. 7 depicts the construction of the plasmid (PBGH 33-3) harboring the gene for BGH comprising the synthetic proximal portion as shown in FIG. 6.

Figure 8:
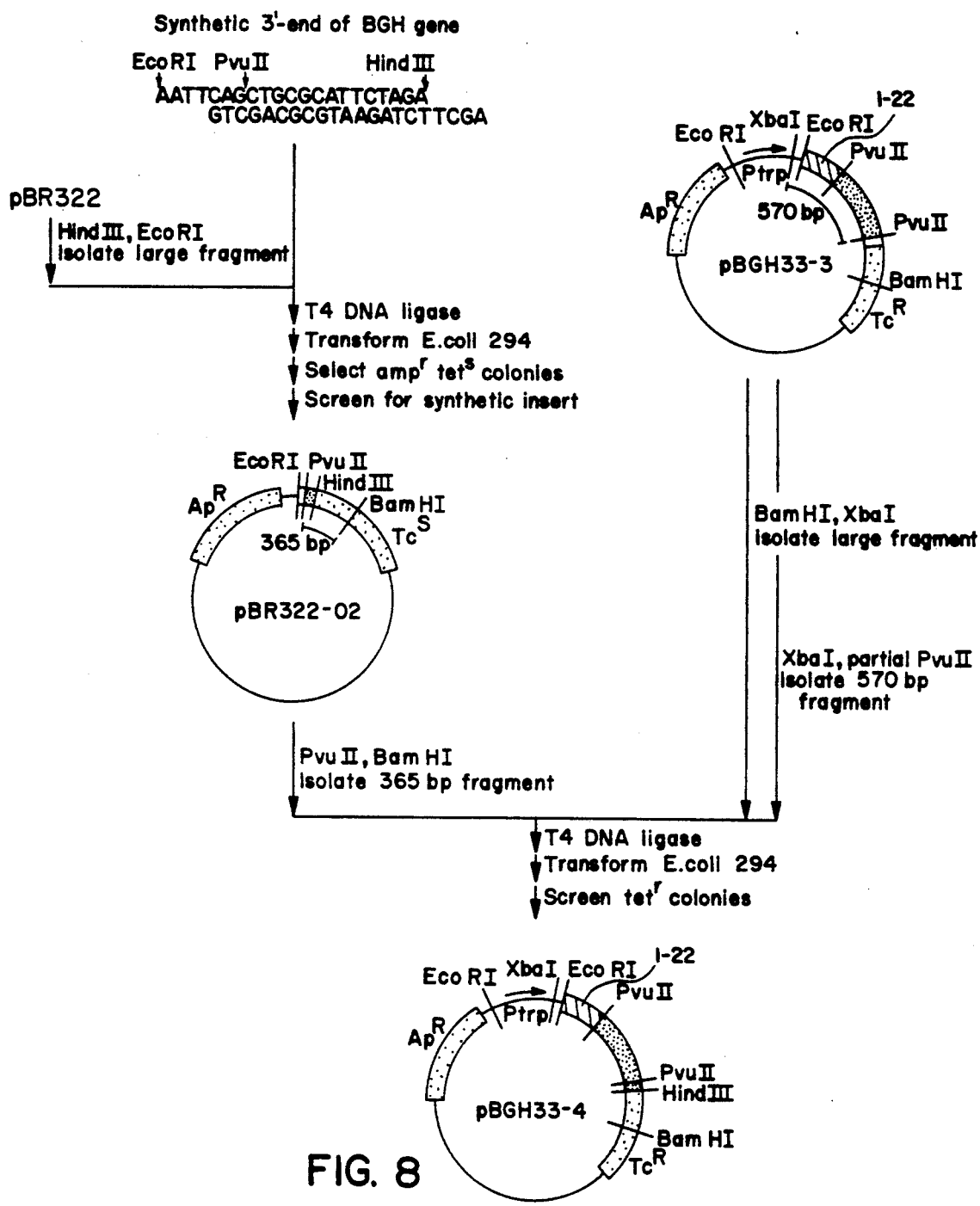

FIG. 8 depicts the construction of expression plasmid PBGH 33-4 harboring the hybrid BGH gene.

Figure 9B:
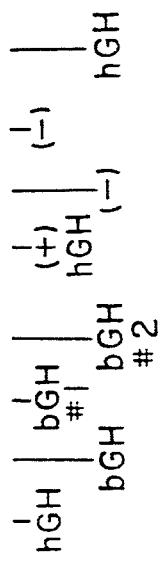
Figure 9A:
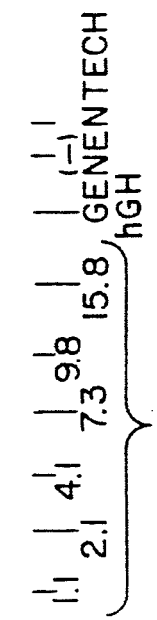

FIG. 9 is the result of a polyacrylamide gel segregation of cell protein. Part A shows no BGH production at any cell density using the culture containing natural BGH gene. Part B shows the expression of synthetic BGH gene (lanes BGH #1 and #2) in the same medium as used for Part A. The levels of expression indicated in Part B, as opposed to Part A, reflect the production of BGH in amounts exceeding about.100 thousand copies per cell.

DESCRIPTION OF PREFERRED EMBODIMENTS

In its most preferred embodiment, the invention is illustrated by the microbial production of bovine growth hormone (BGH). BGH is endogenous in bovine, e.g., cattle, and is responsible for proper physical maturation of the animal. It is also useful for increasing weight gain, feed conversion efficiency, lean to fat ratio, and milk production. Its sequence of 190 amino acids is known. See Dayhoff, *Atlas of Protfin Sequence and Structure* 1972, National Biomedical Research Foundation, Washington, D.C. The present invention makes possible the preparation of commercial quantities of the compound, enabling now its application on a large-scale in the animal husbandry industry. An initial approach toward preparing BGH microbially took advantage of a source of bovine pituitary glands. By extraction and purification, the requisite MRNA for BGH was isolated and from it, corresponding cDNA prepared. Thus, this initial work resulted in a gene corresponding, for all intents and purposes, to the natural DNA sequence of BGH. After removal of DNA coding for the presequence and adding a start codon, the CDNA was ligated to a plasmid vector under proper control of a promotor. This plasmid was used to transform E. coli host which was grown under usual conditions. The efficiency of expression of BGH product was poor, a consequence, it was discovered, of conformational structure of the messenger RNA, which greatly reduced its accessibility for ribosomal translation, cf. FIG. 3.

For example, it was found that in "natural" BGH MRNA there are regions of complementary homology, one significant region centers around positions +46 to +51 with a homologous region at positions 73 to +78, respectively, of the MRNA transcript. Secondary structure considerations, in these two defined regions, are thought to create a hairpin arrangement just downstream from the translation start codon ATG and the ribosome binding site. This conformational arrangement interferes with or prematurely disrupts ribosomal binding, and hence, inhibits translation.

The recognition of this Phenomenon prompted investigations into the nature of the DNA sequence in these regions and the discovery of methods and means to obviate the problem. In accordance herewith, advantage was taken of a PvuII endonuclease restriction site at the BGH DNA corresponding to amino acid 24. DNA for the first 24 amino acids of BGH were chemically synthesized, the selection of nucleotides taking into strict account proper coding sequence and resultant MRNA secondary/ tertiary structure considerations.

Employing the method defined above, it was found that certain nucleotide base selections would be suitable, on the basis of predicted conformational structure energy levels, to prepare gene sequences properly encoding BGH but devoid of problematic conformational structure. One of these was selected and synthesized. Ligations at the Pvu II terminus of the synthetic piece to the CDNA downstream therefrom produced the desired hybrid gene. Construction of a replicable expression vector containing said heterologous gene as an operable insert successfully resulted in efficient expression of BGH in transformed E. coli host.

The complete nucleotide (and deduced amino acid) sequence of the thus constructed hybrid BGH gene is as follows:

| | 1 | | | | | | | | | | | | | |
|---|---|---|---|---|---|---|---|---|---|---|---|---|---|---|
| met | phe | pro | ala | met | ser | leu | ser | gly | leu | phe | ala | asn | ala | val |
| ATG | TTC | CCA | GCT | ATG | TCT | CTA | TCT | GGT | CTA | TTC | GCT | AAC | GCT | GTT |

| | | | | | 20 | | | | | | | | | |
|---|---|---|---|---|---|---|---|---|---|---|---|---|---|---|
| leu | arg | ala | gln | his | leu | his | gln | leu | ala | ala | asp | thr | phe | lys |
| CTT | CGT | GCT | CAG | CAT | CTT | CAT | CAG | CTG | GCT | GCT | GAC | ACC | TTC | AAA |

| | | | | | | | | | | 40 | | | | |
|---|---|---|---|---|---|---|---|---|---|---|---|---|---|---|
| glu | phe | glu | arg | thr | tyr | ile | pro | glu | gly | gln | arg | tyr | ser | ile |
| GAG | TTT | GAG | CGC | ACC | TAC | ATC | CCG | GAG | GGA | CAG | AGA | TAC | TCC | ATC |

| gln | asn | thr | gln | val | ala | phe | cys | phe | ser | glu | thr | ile | pro | ala |
|---|---|---|---|---|---|---|---|---|---|---|---|---|---|---|
| CAG | AAC | ACC | CAG | GTT | GCC | TTC | TGC | TTC | TCT | GAA | ACC | ATC | CCG | GCC |

| 60 | | | | | | | | | | | | | | |
|---|---|---|---|---|---|---|---|---|---|---|---|---|---|---|
| pro | thr | gly | lys | asp | glu | ala | gln | gln | lys | ser | asp | leu | glu | leu |
| CCC | ACG | GGC | AAG | GAT | GAG | GCC | CAG | CAG | AAA | TCA | GAC | TTG | GAG | CTG |

| | | | | | 80 | | | | | | | | | |
|---|---|---|---|---|---|---|---|---|---|---|---|---|---|---|
| leu | arg | ile | ser | leu | leu | leu | ile | gln | ser | trp | leu | gly | pro | leu |
| CTT | CGC | ATC | TCA | CTG | CTC | CTC | ATC | CAG | TCG | TGG | CTT | GGG | CCC | CTG |

| | | | | | | | | | | 100 | | | | |
|---|---|---|---|---|---|---|---|---|---|---|---|---|---|---|
| gln | phe | leu | ser | arg | val | phe | thr | asn | ser | leu | val | phe | gly | thr |
| CAG | TTC | CTC | AGC | AGA | GTC | TTC | ACC | AAC | AGC | TTG | GTG | TTT | GGC | ACC |

| ser | asp | arg | val | tyr | glu | lys | leu | lys | asp | leu | glu | glu | gly | ile |
|---|---|---|---|---|---|---|---|---|---|---|---|---|---|---|
| TCG | GAC | CGT | GTC | TAT | GAG | AAG | CTG | AAG | GAC | CTG | GAG | GAA | GGC | ATC |

| 120 | | | | | | | | | | | | | | |
|---|---|---|---|---|---|---|---|---|---|---|---|---|---|---|
| leu | ala | leu | met | arg | glu | leu | glu | asp | gly | thr | pro | arg | ala | gly |
| CTG | GCC | CTG | ATG | CGG | GAG | CTG | GAA | GAT | GGC | ACC | CCC | CGG | GCT | GGG |

| | | | | | 140 | | | | | | | | | |
|---|---|---|---|---|---|---|---|---|---|---|---|---|---|---|
| gln | ile | leu | lys | gln | thr | tyr | asp | lys | phe | asp | thr | asn | met | arg |
| CAG | ATC | CTC | AAG | CAG | ACC | TAT | GAC | AAA | TTT | GAC | ACA | AAC | ATG | CGC |

| | | | | | | | | | | 160 | | | | |
|---|---|---|---|---|---|---|---|---|---|---|---|---|---|---|
| ser | asp | asp | ala | leu | leu | lys | asn | tyr | gly | leu | leu | ser | cys | phe |
| AGT | GAC | GAC | GCG | CTG | CTC | AAG | AAC | TAC | GGT | CTG | CTC | TCC | TGC | TTC |

| arg | lys | asp | leu | his | lys | thr | glu | thr | tyr | leu | arg | val | met | lys |
|---|---|---|---|---|---|---|---|---|---|---|---|---|---|---|
| CGG | AAG | GAC | CTG | CAT | AAG | ACG | GAG | ACG | TAC | CTG | AGG | GTC | ATG | AAG |

| 180 | | | | | | | | | 190 | | |
|---|---|---|---|---|---|---|---|---|---|---|---|
| cys | arg | arg | phe | gly | glu | ala | ser | cys | ala | phe | stop |
| TGC | CGC | CGC | TTC | GGG | GAG | GCC | AGC | TGC | GCA | TTC | TAG |

DETAILED DESCRIPTION

Synthesis of Proximal Portion of BC-H Gene

Twelve fragments, U 1-6 (upper strand) and L 1-6 (lower strand), were synthesized. Also synthesized, in order to repair the 3' end of the gene, were 2 fragments, BGH Repair (1) (upper strand) and BGH Repair (2) (lower strand).

The 14 fragments were synthesized according to the method of Crea et al., Nucleic Acids Research, 8, 2331 (1980). The syntheses of the fragments were accomplished from the appropriate solid support (cellulose) by sequential addition of the appropriate fully protected dimer - or trimer- blocks. The cycles were carried out under the same conditions as described in the synthesis of oligothymidilic acid (see Crea et al., Supra.) The final polymer was treated with base (aq. conc NH₃) and acid (80% aq. HOAC), the polymer pelleted off and the supernatant evaporated to dryness. The residue, as dissolved in 4% aq. NH₃, was washed with ether (3x) and used for the isolation of the fully deprotected fragment. Purification was accomplished on hplc on Rsil NH₂ unparticulate column. Gel electrophoretic analysis showed that each of the fragments, U,L 1-6 and BGH Repair (1) and (2), had the correct size:

| Fragment | Sequence | Size |
|---|---|---|
| U 1 | 5' AAT.TCT.ATG.TTC.C3' | 13-mer |
| U 2 | 5' CAG.CTA.TGT.CTC.T3' | 13-mer |
| U 3 | 5' ATC.TGG.TCT.ATT.C3' | 13-mer |
| U 4 | 5' GCT.AAC.GCT.GTT.C3' | 13-mer |
| U 5 | 5' TTC.GTG.CTC.AGC.A3' | 13-mer |
| U 6 | 5' TCT.TCA.TCA.GCT.GA3' | 14-mer |
| L 1 | 5' ATA.GCT.GGG.AAC.ATA.G3' | 16-mer |
| L 2 | 5' ACC.AGA.TAG.AGA.C3' | 13-mer |
| L 3 | 5' CGT.TAG.CGA.ATA.G3' | 13-mer |
| L 4 | 5' GCA.CGA.AGA.ACA.G3' | 13-mer |
| L 5 | 5' ATG.AAG.ATG.CTG.A3' | 13-mer |
| L 6 | 5' AGC.TTC.AGC.TG3' | 11-mer |
| BGH Repair (1) | 5' AA.TTC.AGC.TGC.GCA.TTC.TAG.A3' | 21-mer |
| BGH Repair (2) | 5' AG.CTT.CTA.GAA.TGC.GCA.GCT.G3' | 21-mer |

Construction of PBGH 33

Fresh frozen bovine pituitaries were maserated and RNA was extracted by the guanidium thiocyarate method. (Harding et al., J. Biol Chem. 252 (20), 7391 (1977) and Ullrich et al., Science 196, 1313 (1977)). The total RNA extract was then passed over an oligo-dt cellulose column to purify poly A containing messenger RNA (mRNA). Using reverse transcriptase and oligo-dt as a primer, single stranded CDNA was made from the MRNA. Second strand synthesis was achieved by use of the Klenow fragment of DNA polymerase I. Following S1 enzyme treatment and acrylamide gel electrophoresis a size cut of the total CDNA (ca. 500-1500 bp) was eluted and cloned into the Pst I site of the amp$^R$ gene of pBR 322 using traditional tailing and annealing conditions.

The pBR 322 plasmids containing CDNA were transformed into E. coli K-12 strain 294 (ATCC No. 31446). Colonies containing recombinant plasmids were selected by their resistance to tetracycline and sensitivity to ampicillin. Approximately 2000 of these clones were screened for BGH by colony hybridization.

The CDNA clones of HGH contain an internal 550 bp HaeIII fragment. The amino acid sequence of this region is very similar to the BGH amino acid sequence. This HGH HaeIII fragment was radioactively labeled and used as a probe to find the corresponding BGH sequence amongst the 2000 clones.

Eight positive clones were identified. One of these, pBGH112, was verified by sequence analysis as BGH. This full-length clone is 940 bp long containing the coding region of the 26 amino acid presequence as well as the 191 amino acid protein sequence.

In order to achieve direct BGH expression, a synthetic "expression primer" was made having the sequence 5'-ATGTTCCCAGCCATG-3'. The nucleotides in the fourth through fifteenth position are identical to the codons of the first 4 amino acids of the mature BGH protein, as determined by sequence data of PBGH 112. Only the 5' ATG (methionine) is alien to this region of the protein. This was necessary in order to eliminate the presequence region of our BGH clone and to provide the proper initiation codon for protein synthesis. By a series of enzymatic reactions this synthetic primer was elongated on the BGH 112 CDNA insert. The primed product was cleaved with Pst I to give a DNA fragment of 270 bp containing coding information up to amino acid 90. (FIG. 4) This "expression" BGH CDNA fragment was ligated into a pBR 322 vector which contained the trp promotor. This vector was derived from pLeIF A trp25 (Goeddel et al., Nature 287, 411 (1980)). The interferon CDNA was removed and the trp25-322 vector purified by gel electrophoresis. The recombinant plasmid (pBGH710) now contained the coding information for amino acids 1-90 of the mature BGH protein, linked directly to the trp promotor. This linkage was verified by DNA sequence analysis. The second half of the coding region and the 3' untranslated region was isolated from pBGH112 by PstI restriction digest and acrylamide gel electrophoresis. This "back-end" fragment of 540 bp was then ligated into pBGH710 at the site of amino acid 90. Recombinant plasmids were checked by restriction analysis and DNA sequencing. 7he recombinant plasmid, pBGH33, has the trp promotor directly linked via ATG with the complete DNA coding sequence for mature BGH.

Construction of PHGH 207-1

Plasmid pGM1 carries the E. coli tryptophan operon containing the deletion LE1413 (G.F. Miozzari, et al., (1978) J. Bacteriology 1457-1466)) and hence expresses a fusion protein comprising the first 6 amino acids of the trp leader and approximately the last third of the trp E polypeptide (hereinafter referred to in conjunction as LE'), as well as the trp D polypeptide in its entirety, all under the control of the trp promoter-operator system. The plasmid, 20 ug, was digested with the restriction enzyme PvuII which cleaves the plasmid at five sites. The gene fragments were next combined with EcoRI linkers (consisting of a self complementary oligonucleotide of the sequence: PCATGAATTCATG) providing an EcoRI cleavage site for a later cloning into a plasmid containing an EcoRI site. The 20 ug of DNA fragments obtained from pGM1 were treated with 10 units T₄ DNA ligase in the presence of 200 pico moles of the 5'-phosphorylated synthetic oligonucleotide PCATGAATTCATG and in 20ul T₄ DNA ligase buffer (20mM tris, pH 7.6, 0.5 MM ATP, 10 mM MgCl₂, 5 mM dithiothreitol) at 4° C. overnight. The solution was then heated 10 minutes at 70° C. to inactivate ligase. The linkers were cleaved by EcoRI digestion and the fragments, now with EcoRI ends were separated using polyacrylamide gel electrophoresis (hereinafter "PAGE") and the three largest fragments isolated from the gel by first staining with ethidium bromide, locating the fragments with ultraviolet light, and cutting from the gel the portions of interest. Each gel fragment, with 300 microliters 0.1×TBE, was placed in a dialysis bag and subjected to electrophoresis at 100 V for one hour in 0.1×TBE buffer (TBE buffer contains: 10.8 gm tris base, 5.5 gm boric acid, 0.09 gm Na$_2$EDTA in 1 liter H$_2$O). The aqueous solution was collected from the dialysis bag, phenol extracted, chloroform extracted and made 0.2 M sodium chloride, and the DNA recovered in water after ethanol precipitation. (All DNA fragment isolations hereinafter described are performed using PAGE -Hollowed by the electroelution method just discussed.) The trp promoter-operator-containing gene with EcoRl sticky ends was identified in the procedure next described, which entails the insertion of fragments into a tetracycline sensitive plasmid which, upon promoter-operator insertion, becomes tetracycline resistant.

Plasmid PBRHI, (R.I. Rodriguez, et al., Nucleic Acids Research 6, 3267–3287[1979j) expresses ampicilin resistance and contains the gene for tetracycline resistance but, there being no associated promoter, does not express that resistance. The plasmid is accordingly tetracycline sensitive. By introducing a promoter-operator system in the EcoRl site, the plasmid can be made tetracycline resistant.

pBRHI was digested with EcoRl and the enzyme removed by phenol/CHCl$_3$ extraction followed by chloroform extraction and recovered in water after ethanol precipitation. The resulting DNA molecule was, in separate reaction mixtures, combined with each of the three DNA fragments obtained as described above and legated with T$_4$ DNA ligase as previously described. The DNA present in the reaction mixture was used to transform competent E. coli K-12 strain 294 (K. Beckman et al., Proc Nat'l Acad Sci USA 73, 4174–4198 (1976) (ATCC no. 31446) by standard techniques (V. Hershfield et al., Proc Nat'l Acad Sci USA 71, 3455–3459 (1974) and the bacteria plated on LB plates containing 20 ug/ml ampicillin and 5 ug/ml tetracycline. Several tetracycline-resistant colonies were selected, plasmid DNA isolated and the presence of the desired fragment confirmed by restriction enzyme analysis. The resulting plasmid, designated pBRHtrp, expresses β-lactamase, imparting ampicillin resistance, and it contains a DNA fragment including the trp promoter-operator and encoding a first protein comprising a fusion of the first six amino acids of the trp leader and approximately the last third of the trp E polypeptide (this polypeptide is designated LE'), and a second protein corresponding to approximately the first half of the trp D polypeptide (this polypeptide is designated D'), and a third protein coded for by the tetracycline resistance gene.

pBRH trp was digested with EcoRI restriction enzyme and the resulting fragment 1 isolated by PAGE and electroelution. EcoRI-digested plasmid psom 11 (K. Itakura et al, Science 198, 1056 (1977) was combined with this fragment 1. The mixture was legated with T$_4$DNA ligase as previously described and the resulting DNA transformed into E. coli K-12 strain 294 as previously described. Transformant bacteria were selected on ampicillin-containing plates. Resulting ampi-cillin-resistant colonies were screened by colony hybridization (M. Gruenstein St al., Proc Nat'l Acad Sci USA 72, 3951–3965[19751]) using as a probe the trp promoter-operator-containing fragment 1 isolated from pBRHtrp, which had been radioactively labelled with P$^{32}$. Several colonies shown positive by colony hybridization were selected, plasmid DNA was isolated and the orientation of the inserted fragments determined by restriction analysis employing restriction enzymes Bglll and BamHI in double digestion. E. coli 294 containing the plasmid designated pSOM7Δ2, which has the trp promoter-operator fragment in the desired orientation was grown in LB medium containing 10 μg/ml ampicillin. The cells were grown to optical density 1 (at 550 NM), collected by centrifugation and resuspended in M9 media in tenfold dilution. Cells were grown for 2–3 hours, again to optical density 1, then lysed and total cellular protein analyzed by SDS (sodium dodcyl sulfate) area (15 percent) polyacrylamide gel electrophoresis (J.V. Maizel Jr. et al., Meth Viral 5, 180–246 (1971)).

The plasmid pSom7Δ2, lopg, was cleaved with EcoRI and the DNA fragment 1 containing the tryptophan genetic elements was isolated by PAGE and electroelution. This fragment, 2μg, was digested with the restriction endonuclease Taq I, 2 units, 10 minutes at 37° C. such that, on the average, only one of the approximately five Taq I sites in each molecule is cleaved. This partially digested mixture of fragments was separated by PAGE and an approximately 300 base pair fragment 2 that contained one EcoRI end and one Taq I end was isolated by electroelution. The corresponding Taq I site is located between the transcription start and translation start sites and is 5 nucleotides upstream from the ATG codon of the trp leader peptide. The DNA sequence about this site is shown in FIG. 4. By proceeding as described, a fragment could be isolated containing all control elements of the trp operon, i.e., promoter-operator system, transcription initiation signal, and part of the trp leader ribosome binding site.

The Taq I residue at the 3' end of the resulting fragment adjacent the translation start signal for the trp leader sequence was next converted into an XbaI site. This was done by ligating the Fragment 2 obtained above to a plasmid containing a unique (i.e., only one) EcoRI site and a unique XbaI site. For this purpose, one may employ essentially any plasmid containing, in order, a replicon, a selectable marker such as antibiotic resistance, and EcoRI, XbaI and BamHI sites. Thus, for example, an XbaI site can be introduced between the EcoRI and EamHI sites cf pBR322 (F. Bolivar et al., Gene 2, 95–119[19771]) by, e.g., cleaving at the plasmid's unique Hind Ill site with Hind III followed by single strand-specific nuclease digestion of the resulting sticky ends, and blunt end ligation of a self annealing double-stranded synthetic nucleotide containing the recognition site such as CCTCTAGAGG. Alternatively, naturally derived DNA fragments may be employed, as was done in the present case, that contain a single XbaI site between EcoRI and BamHl cleavage residues. Thus, an EcoRI and BamHI digestion product of the viral genome of hepatitis B was obtained by conventional means and cloned into the EcoRI and BamHI sites of plasmid pGH6 (D.V. Goeddel et al., Nature 281, 544[1979])) to form the plasmid pHS32. Plasmid pHS32 was cleaved with XbaI, phenol extracted, chloroform extracted and ethanol precipitated, it was then treated with 1 ul E. coli polymerase 1, Klenow fragment (Boehringer-Mannheim) in 30 ul polymerase buffer (50 mM potassium phosphate pH 7.4, 7mM MgCl$_2$, 1 mm β-mercaptoethanol) containing 0.1MM DTTP and 0.1mm DCTP for 30 minutes at 0° C. then 2 hr. at 37° C. This treatment causes 2 of the 4 nucleotides complementary to the 5' protruding end of the XbaI cleavage site to be filled in:

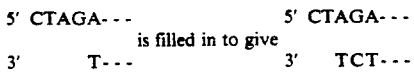

Two nucleotides, dC and dT, were incorporated giving an end with two 5' protruding nucleotides. This linear residue of plasmid pHS32 (after phenol and chloroform extraction and recovery in water after ethanol precipitation) was cleaved with EcoRI. The large plasmid Fragment was separated from the smaller EcoRI-XbaI fragment by PAGY and isolated after electroelution. This DNA fragment from pHS32 (0.2 ug), was ligated, under conditions similar to those described above, to the EcoRI-Taq I fragment of the tryptophan operon ( 0.01 ug). In this process the Taq I protruding end is ligated to the XbaI remaining protruding end even though it is not completely Watson-Crick basepaired:

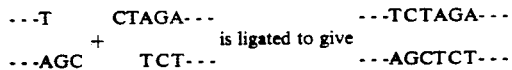

A portion of this ligation reaction mixture was transformed into E. coli 294 cells as in part I. above,, heat treated and plated on LB plates containing ampicillin. Twenty-four colonies were selected, grown in 3 ml LB media, and plasmid isolated. Six of these were found to have the XbaI site regenerated via E. coli catalyzed DNA repair and replication:

These plasmids were also found to cleave both with EcoRI and HpaI and to give the expected restriction fragments. One plasmid 14, designated ptrp 14, was used for expression of heterologous polypeptides, as next discussed.

The plasmid PHGH 107 (D.V. Goeddel et al, Nature, 281, 544, 1979) contains a gene for human growth hormone made up of 23 amino acid codons produced from synthetic DNA fragments and 163 amino acid codons obtained from complementary DNA produced via reverse transcription of human growth hormone messenger RNA. This gene, 3, though it lacks the codons of the "pre" sequence of human growth hormone, does contain an ATG translation initiation codon. The gene was isolated from 10 ug PHGH 107 after treatment with EcoRI followed by E. coli polymerase I Klenow fragment and DTTP and DATP as described above. Following phenol and chloroform extraction and ethanol precipitation the plasmid was treated with BamHI. The human growth hormone ("HGH") gene-containing fragment 3 was isolated by PAGE followed by electroelution. The resulting DNA fragment also contains the first 350 nucleotides of the tetracycline resistance structural gene, but lacks the tetracyline promoter-operator system so that, when subsequently cloned into an expression plasmid, plasmids containing the insert can be located by the restoration of tetracycline resistance. Because the EcoRI end of the fragment 3 has been filled in by the Klenow polymerase I procedure, the fragment has one blunt and one sticky end, ensuring proper orientation when later inserted into an expression plasmid.

The expression plasmid pTrp14 was next prepared to receive the HGH gene-containing fragment prepared above. Thus, pTrp14 was XbaI digested and the resulting sticky ends filled in with the Klenow polymerase I procedure employing DATP, DTTP, DGTP and dCTP. After phenol and chloroform extraction and ethanol precipitation the resulting DNA was treated with BamHI and the resulting large plasmid fragment isolated by PAGE and electroelution. The pTrp14-derived fragment had one blunt and one sticky end, permitting recombination in proper orientation with the HGH gene containing fragment 3 previously described. The HGH gene fragment 3 and the pTrp14 Xba-BamHI fragment were combined and ligated together under conditions similar to those described above. The filled in XbtI and EcoRI ends ligated together by blunt end ligation to recreate both the XbaI and the EcoRI site:

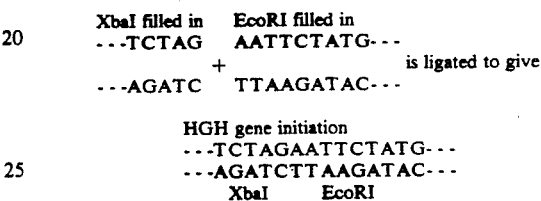

This construction also recreates the tetracycline resistance gene. Since the plasmid PHGH 107 expresses tetracycline resistance from a promoter lying upstream from the HGH gene (the lac promoter), this construction, designated PHGH 207, permits expression of the gene for tetracycline resistance under the control of the tryptophan promoter-operator. Thus the ligation mixture was transformed into E. coli 294 and colonies selected on LB plates containing 5 ug/ml tetracycline.

Construction of pBGH33-1 (FIG. 5)

The structure of pHGH207-1 which has the entire human growth hormone gene sequence is shown. The front part of this gene is synthetic as is described by Goeddel et al., Nature 281, 544 (1979). In the following a plasmid was constructed containing the BGH gene in the same orientation and in the same position with respect to the trp-promotor as is the HGH gene in PHGH 207-1.

Twenty μl (i.e. lopg) of the plasmid DNA was digested with Bam HI and PvuII as follows: To the twenty μl of DNA we added 5 μl 10X restriction enzyme buffer (500mM NaCl, 100 am Tris HCl pH 7.4, 100 mM MgSO4 and 10 mM YTT), 20 ul H2O and 10 units BamHI restriction enzyme and 2 ul PvuII restriction enzyme. Subsequently, this reaction mixture was incubated at 37° C. for 90 minutes. The mixture was loaded on a 6 percent acrylamide gel and electrophoresis was carried out for2 hours at 50 mA. The DNA in the gel was stained with Ethidium bromide and visualized with UV-light. The band corresponding to the 365 bp (with reference to a HaeIII digest of pBR322) fragment was excised and inserted in a dialysis bag and the DNA was electroeluted using a current of 100 mA. The liquid was removed from the bag and its salt concentration adjusted to 0.3M NaCl. Two volumes of ethanol were added and the DNA precipitated at −70° C. The DNA was spun down in an Eppendorf centrifuge, washed with 70 percent ethanol and dried and resuspended in 10 ul TAE (10 mM Tris HCl pH7.4, 0.1 mM EDTA). Similarly, the large XbaI Bam Hl fragment of PHGH 207-1 and the XbaI, partial PvuII 570 bp fragment of pBGH33 were isolated.

Two μl of each of the thus isolated DNA fragments were mixed. 1 μl 10mM ATP and 1 μl 10x ligase buffer (200 MM Tris HCl pH7.5, 100MM mgcl$_2$, 20 mM DTT) and 1 μl T DNA ligase and 2 μl H$_2$O were added. Ligation was done over night at 4° C. This mixture was used to transform competent E. coli K-12 294 cells as follows: 10 ml L-broth was inoculated with E. coli K-12 294 and incubated at 37° C. in a shaker bath at 37° C. AT OD$_{550}$ of 0.8 the cells were harvested by spinning in a Sorvall centrifuge for 5 min. at 6000 rpm. The cell pellet was washed/resuspended in 0.15 M NaCl, and again spun. The cells were resuspended in 75 mM CaCl$_2$, 5 MM mgcl and 10 mM Tris HCl pH7.8 and incubated on ice for at least 20 min. The cells were spun down for 5 min at 2500 rpm and resuspended in the same buffer. To 250 ul of this cell suspension each of the ligation mixtures was added and incubated for 60 min on ice. The cells were heat shocked for 90 seconds at 42° C., chilled and 2 ml L-broth was added. The cells were allowed to recover by incubation at 37° C. for 1 hour. 100 ul of this cell suspension was plated on appropriate plates which were subsequently incubated over night at 37° C. The plasmid structure in several of the colonies thus obtained is shown in FIG. 5 (PBGH 33-1).

All further constructions were done using the same procedures, as described above, mutatis mutandis.

Construction of the Hybrid Growth Hormone Genes HBGH and BHGH (FIG. 5)

The two PvuII sites in the HGH and BGH genes are at identical positions. Exchange of PvuII fragments is possible without changing the reading frame of the messenger RNA of these genes. The large difference in expression of both genes is due to differences in initiation of protein synthesis at the beginning of the messages. Therefore, the front part of both genes were exchanged thus constructing hybrid genes that upon transcription would give hybrid messenger RNAS. The two plasmids, PBHGH and pHBGH, were constructed as follows:

From PHGH207-1 there were isolated the large BamHI-XbaI fragment and the 857 bp lamHI (partial) PvuII fragment containing the HGH gene without its front part. From pBGH33-1 there was isolated the 75 bp XbaI-PvUII fragment that contains the front part of the BGH gene. After ligation and transformation PBHGH was obtained. pHBGH was constructed in a similar way as PBHGH; in this case the back part was derived from pBGH33-1 whereas the front part, the 75 bp XbaI-PvuII fragment, was derived from pHGH207-1.

Design and Cloning of the Synthetic Front Part of the BGH Gene (FIG. 6)

The DNA sequence up to the PvuII si-e of the BGH and HGH gene codes for 22 amino acids. Since the front part of the HGH gene had excellent protein synthesis initiation properties, the sequence of the front part of BGH was designed such that the number of nucleotide changes in the BGH gene would be minimal with respect to the HGH gene. Only 14 base pair changes from the natural BGH sequence were made in order to code for the proper BGH amino acid sequence and reduce conformational structure in the prospective MRNA. The DNA sequence is shown in FIG. 6. The sequence ends with EcoRI and HindIII sticky ends to make cloning in a vector easy. Close to the HindIII site is a PvuII site for the proper junction with the remaining part of the BGH gene.

The fragments U1 to U6 and L1 to L6 were synthesized chemically according to the procedures described above. All the fragments except U1 and L6 were mixed and kinased. After addition of U1 and L6 the mixed fragments were ligated, purified on a 6 percent polyacrylamide gel and the 75 bp band extracted and isolated according to standard procedures. This fragment was inserted into pBR322 that had been cut with EcoRI and HindIII. Thus plasmid pBR322-01 was obtained.

Replacement of the Natural Front Part of the BGH Gene by the Synthetic Front Part. (FIG. 7)

From pBR322-01 the cloned synthetic front of the BGH gene was excised with EcoRI and PvuII, and the resulting 70 bp fragment was isolated. From pBGR33-1 the large EcoRl-BaMBI fragment and the 875 bp LamHI (partial) PvuII fragment was isolated. The three fragments were isolated and ligated and used to transform E. coli K-12 294 as described before. Thus, pBGH33-2 was obtained. This plasmid contains the entire BGH gene but does not have a promotor. Therefore, pEZH33-2 was cut with EcoRI and the trp-promotor containing 310 bp EcoRI fragment derived from pHGH207-1 was inserted by ligation. After transformation tetracycline resistant colonies were analyzed. Therefore, these colonies had the inserted trp-promotor oriented towards the HGH- and tet-gene as shown in the figure.

Repair of the 3'-end of the BGH Gene (FIG. 8)

The sequences beyond the second PvuII site of the BGH gene are derived from the HGH gene. One of the amino acids at the end is different from that in the natural BGH gene. This 3'-end was repaired as follows. A synthetic DNA fragment as shown was synthesized. It is flanked by an EcoRI and a HindIII end to facilitate cloning and contains a PvuII site and 3 amino acid codons and a stop codon in the reading frame of the BGH gene itself. This fragment was inserted into EcoRI-HindIII opened pBR322. Thus pBR322-02 was obtained. Subsequently this plasmid was cut with PvuII and BamHI and the 360 bp fragment was isolated. From pBGH33-3, which has the entire BGH gene with the synthetic front part, the large BamHI and XbaI fragment and the 570 bp XbaI (partial) PvuII fragment was isolated. These three fragments were ligated and used to transform cells. Thus, pBGH33-4 was obtained. In this plasmid a unique HindIII site is present between the stop codon of the BGH gene and the start codon of the tet-mRNA. Both genes are transcribed under direction of the promotor.

A typical growth medium used to derepress and produce high levels of BGH per liter (FIG. 9) contains: 5.0 g (NH$_4$)$_2$SO$_4$, 6.0 g K$_2$HPO$_4$, 3.0 g NaH$_2$PO$_4$.2H$_2$O, 1.0 g sodium citrate, 2.5 g glucose, 5 ag tetracycline, 70 mg thiamine HCl, and 60 g MgSO$_4$.7H$_2$O.

While the present invention has been described, in its preferred embodiments, with reference to the use of E. coli transformants, it will be appreciated that other microorganisms can be employed mutatis mutandis. Examples of such are other E. coli organisms, e.g, E. coli B., E. coli W3110 ATCC No. 31622 (F$^-$, λ$^-$, gal$^-$, prototroph), E. coli x 1776, ATCC No. 31537, E. coli D1210, E. coli RV308, ATCC No. 31608, etc., Bacillus subtilis strains, Pseudomonas strains, etc. and various yeasts, e.g., Saccharomyces cerevisiae many of which are deposited and (potentially) available from recognized depository institutions e.g., ATCC. Following the practice of this invention and the final expression of intended polypeptide product, extraction and purification techniques are those customarily employed in this art, known per se.

We claim:

1. A method comprising culturing a microbial cell containing DNA encoding a bovine growth hormone from which the presequence has been eliminated and wherein the messenger RNA transcribed from the DNA (a) contains at least a translational start signal and an N-terminal portion encoding the bovine growth hormone and (b) within the region from nucleotide +1 to +100 is free of secondary structure having a thermodynamic energy arithmetically less than or equal to the thermodynamic energy of the secondary structure formed by homologous base pairing between nucleotides 46 to 51 and nucleotides 73 to 78 of the native messenger RNA encoding BGH.

2. The method of claim 1 wherein the bovine growth hormone consists of a natural, mature bovine growth hormone having an N-terminal methionyl.

3. The method of claim 2 wherein the first nucleotide of the DNA corresponds to nucleotide +1 of the corresponding messenger RNA.

4. The method of claim 2 wherein the first nucleotide of the DNA corresponds to nucleotide +1 of the corresponding messenger RNA and the DNA extends through at least the last nucleotide of the codon encoding the last of about the proximal 25 amino acids of the bovine growth hormone.

5. The method of claim 2 wherein the DNA extends from the nucleotide +1 to about nucleotide +100 of the corresponding messenger RNA.

6. The method of claim 2 wherein the microbial cell is *E. coli*.

7. The method of claim 2 wherein the DNA is transcribed under the direction of the trp promoter.

8. The method of claim 2 wherein the DNA was synthesized in vitro.

9. The method of claim 2 wherein the DNA was prepared by site directed mutagenesis.

10. The method of claim 2 wherein the messenger RNA encodes the about 25 N-terminal amino acids of the bovine growth hormone.

11. The method of claim 2 wherein the messenger RNA contains a ribosomal binding site in addition to the start codon and the N-terminal portion of the bovine growth hormone.

12. The method of claim 2 wherein the DNA encodes bovine growth hormone having the N-terminal sequence Met Phe Pro Ala Met Ser Leu Ser Gly Leu Phe Ala Asn Ala Val Leu Arg Ala Gln His Leu His Gln.

13. The method of claim 2 wherein the cell is grown in cell culture medium and caused to produce the bovine growth hormone, and the method further comprises recovering the bovine growth hormone from the medium.

14. The method of claim 13 wherein the cell contains bovine growth hormone in an amount exceeding about 100 thousand copies.

15. The method of claim 13 wherein the bovine growth hormone contains the N-terminal sequence Met Phe Pro Ala Met Ser Leu Ser Gly Leu Phe Ala Asn Ala Val Leu Arg Ala Gln His Leu His Gln.

16. A method which comprises growing in cell culture medium a microorganism containing a DNA operably linked to a promoter which controls expression of the DNA in said microorganism, which DNA:
(a) encodes a polypeptide comprising the amino acid sequence of a natural bovine growth hormone; and
(b) includes a translation initiation codon directly linked to the end of the DNA encoding said hormone; wherein the nucleotides in said DNA that have been selected to encode the about 25 N-terminal amino acids of said hormone differ from the corresponding nucleotides in the naturally occurring gene encoding said hormone by providing, on transcription of said DNA, messenger RNA which on translation, produces a higher level of bovine growth hormone ion the microorganism that is produced from the messenger RNA encoded by said naturally occurring gene.

17. A method of claim 16 wherein the microorganism is bacterial.

18. A method of claim 16 wherein the microorganism is *E. coli*.

19. A method of claim 16 wherein the *E. coli* is a K-12 strain.

20. A method of claim 16 wherein the messenger RNA encoded by the DNA, within the region from nucleotide +1 to about +100, is free of secondary structure having a thermodynamic energy arithmetically less than or equal to the thermodynamic energy of the secondary structure formed by homologous base pairing between nucleotides 46 to 51 and nucleotides 73 to 78 of the messenger RNA encoded by said naturally occurring gene.

21. A method of claim 16 wherein the nucleotides of said synthetic DNA that encode the alanine within the proline-alanine-methionine sequence near the N-terminus of the hormone are GCT.

22. A method of claim 16 which comprises causing expression of said synthetic DNA in the microorganism and recovering the resulting bovine growth hormone.

23. A method of claim 22 in which bovine growth hormone is expressed in amounts exceeding about 100,000 copies per cell.

24. A method which comprises growing in cell culture medium *E. coli* containing a DNA operably linked to a promoter which controls expression of the DNA in said *E. coli*, which DNA:
(a) encodes a polypeptide comprising the amino acid sequence of a natural bovine growth hormone; and
(b) includes a translation initiation codon directly linked to the end of the DNA encoding said hormone; wherein the nucleotides in said DNA that have been selected to encode the alanine within the proline-alanine-methionine sequence near the N-terminus of the hormone at, resulting in the messenger RNA transcribed from said DNA having secondary structure which interferes less than the secondary structure of the corresponding naturally occurring messenger RNA with ribosomal translation of such messenger RNA in *E. coli*.

25. A method of claim 24 which comprises causing expression of said synthetic DNA to produce bovine growth hormone in the *E. coli* in amounts exceeding about 100,000 copies per cell, and recovering the resulting bovine growth hormone.

26. A method of claim 25 wherein the *E. coli* is a K-12 strain.

* * * * *